United States Patent [19]

Luhrs et al.

[11] Patent Number: 4,749,480

[45] Date of Patent: Jun. 7, 1988

[54] REACTION VESSEL

[75] Inventors: Hermann Luhrs, Grevenbroich; Jürgen Preetz, Wolfersheim, both of Fed. Rep. of Germany

[73] Assignee: Sulzer Brothers Limited, Winterthur, Switzerland

[21] Appl. No.: 797,425

[22] Filed: Nov. 12, 1985

[30] Foreign Application Priority Data

Nov. 20, 1984 [CH] Switzerland .................... 5531/84

[51] Int. Cl.$^4$ ............................................. C02F 11/04
[52] U.S. Cl. .................................. 210/188; 210/195.4; 210/261; 210/521
[58] Field of Search ............ 210/603, 180, 188, 195.4, 210/261, 521, 539, 195.3

[56] References Cited

U.S. PATENT DOCUMENTS

| 3,239,067 | 3/1966 | Hikes et al. | 210/521 |
| 4,346,005 | 8/1982 | Zimmerman | 210/521 X |
| 4,372,856 | 2/1983 | Morrison | 210/180 X |
| 4,530,762 | 7/1985 | Love | 210/539 X |
| 4,594,078 | 6/1986 | Guerin et al. | 210/180 X |

Primary Examiner—Tom Wyse
Attorney, Agent, or Firm—Kenyon & Kenyon

[57] ABSTRACT

The reaction vessel is provided with a partition to separate a sub-chamber from the reaction chamber of the vessel. The sub-chamber also contains lamellar flowbacks for the separation of liquid and biomass. Clean liquid is collected in troughs at the top end inside of the flowbacks and is transported via a circular trough to a discharge spigot. Biomass is discharged via sludge pockets which open directly into the reaction chamber.

19 Claims, 4 Drawing Sheets

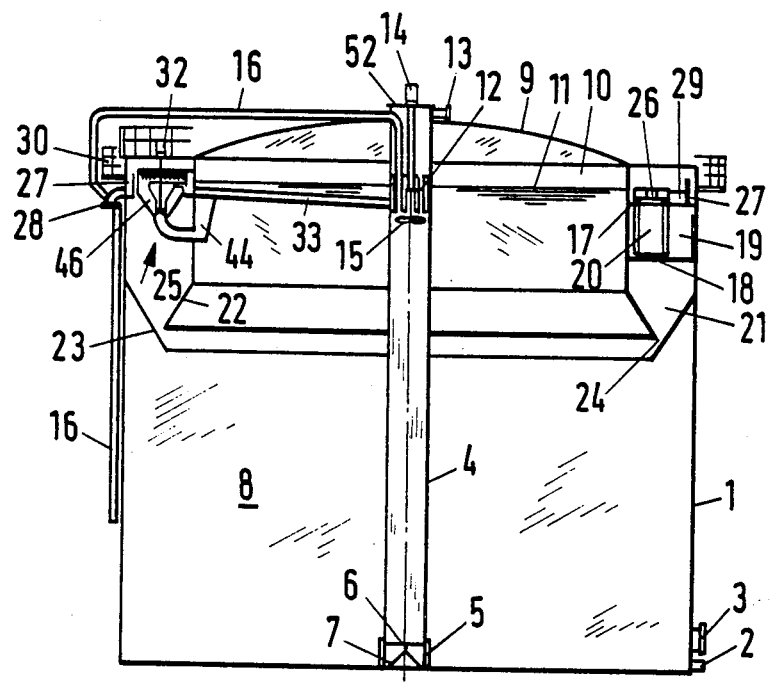
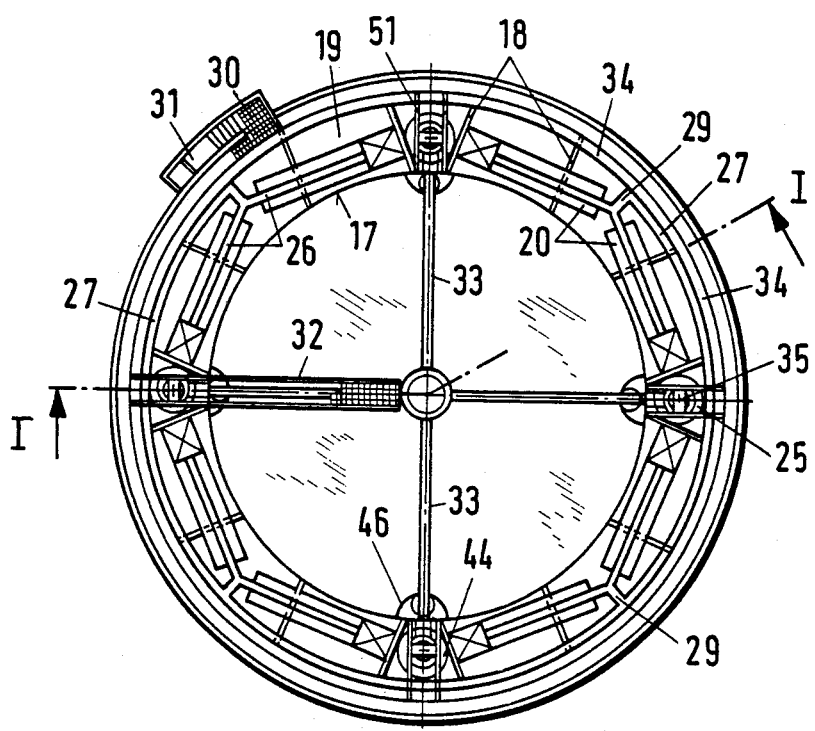

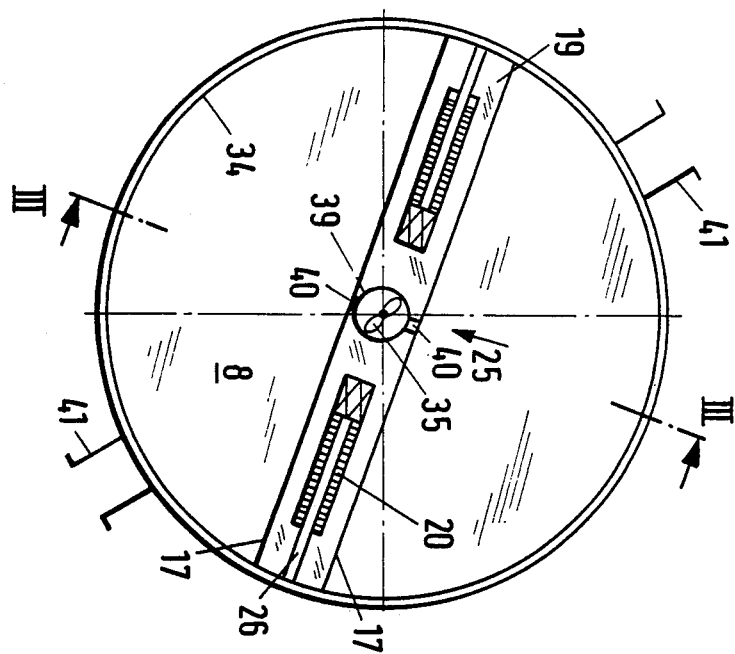
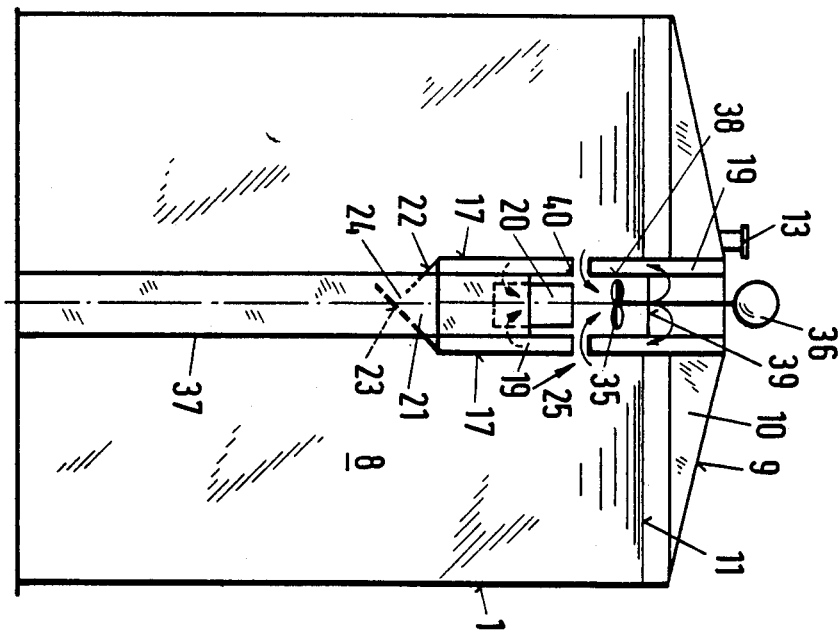

REACTION VESSEL

This invention relates to a reaction vessel. More particularly, this invention relates to a reaction vessel for anaerobic treatment of contaminated liquid such as sewage.

Heretofore, various types of reaction vessels have been proposed for the anaerobic treatment of contaminated liquids such as sewage. In many cases, such as described in European Patent No. 0058247, such reaction vessels employ a methane reactor for the anaerobic treatment in which a gas chamber which is sealed off from the environment is disposed above a reaction chamber. In addition, a packed bed has been used as a separating means in order to separate a liquid from a biomass at the end of the reaction chamber. However, this separation of the liquid from the biomass requires additional means for backwashing and cleaning of the packed bed. This, in turn, leads to additional costs and additional components.

Accordingly, it is an object of the invention to provide a reaction vessel in which the separation of gas, liquid and biomass are integrated within a reaction chamber.

It is another object of the invention to provide a compact unit for the anaerobic treatment of contaminated liquids.

It is another object of the invention to simplify the construction of a reaction vessel for the anaerobic treatment of contaminated liquids.

It is another object of the invention to eliminate a need for a separate means for separating the components of an anaerobically treated contaminated liquid in a reaction vessel.

Briefly, the invention provides a reaction vessel for anaerobic treatment of contaminated liquids which comprises a reaction chamber for receiving contaminated liquid and a gas chamber above the reaction chamber which is sealed from the surrounding environment for receiving gas evolved from the contaminated liquid in the reaction chamber. In accordance with the invention, a sub-chamber is disposed within the vessel for receiving a mixture of liquid and biomass from the reaction chamber. This sub-chamber is located adjacent an interface between the reaction chamber and the gas chamber while a partition separates the sub-chamber from the reaction chamber.

In addition, a means in the form of at least one lamellar flowback is provided in the sub-chamber for separating biomass from the liquid in the mixture delivered to the sub-chamber. The use of the lamellar flowback eliminates the need for regular backwashing and the associated components.

A feed means is also provided for delivering contaminated liquid into the reaction vessel. Advantageously, in one embodiment, the feed means includes a central supply or circulating tube which extends into and communicates with the reaction chamber at opposite ends as well as circulating means in the tube for circulating the liquid through the tube. This feed means allows for an improved mixing of the contents of the reaction chamber, that is, the liquid to be processed and the biomass-interspersed liquid in the reaction chamber.

In order to permit supervision and maintenance of the lamellar flowbacks, the sub-chamber is open (to the surrounding environment) and accessible at a top end.

In order to provide for a gentle return of the separated biomass into the reaction chamber, a plurality of funnel-shaped sludge pockets separate a bottom end of the sub-chamber from the reaction chamber. Each of these pockets further has sludge return orifices which communicate directly with the reaction chamber.

The "drive" for circulating the treated liquid through the lamellar flowbacks can be produced in the simplest way be density differences in the reaction chamber and in the liquid which are arrived by the partial degassing of the mixture through the free level surface (interface) of the reaction chamber and by separation of the biomass solids in the lamellar flowbacks. If this drive is inadequate, at least one means may be provided for conveying and distributing the liquid/biomass mixture from the reaction chamber to the lamellar flowbacks. The use of such a conveying means enables the internal circulation in the reaction vessel to be metered and controlled. Further, the capacity of the conveying means, for example in the form of a propeller, may be variable or adjustable, for example, through the agency of a speed control or through restrictors in a conveyor intake. This permits a uniform defined charging of the lamellar flowbacks to be obtained during operation. Advantageously, the defined charging or loading may vary between a quantity equal to the quantity of inflowing liquid and twice this quantity.

A surface sludge separator may also be disposed downstream of the conveying means for separating surface sludge from the liquid/biomass mixture. In this case, a return tube also extends from the separator to the reaction chamber, for example to a central supply tube, in order to return the separated sludge to the reaction chamber.

Of note, the conveying means provides an additional degassing of the liquid before the liquid passes to the lamellar flowbacks. Further, this degassification is intensified where the conveyor is used with a surface sludge separator. In this latter case, a rotatable clearing device may be disposed concentrically of the sludge separator for mechanical clearing of the separator of surface sludge.

These and other objects and advantages of the invention will become more apparent from the following detailed description taken in conjunction with the accompanying drawings wherein:

FIG. 1 illustrates an axial longitudinal sectional view taken on line I—I of FIG. 2 of a reaction vessel constructed in accordance with the invention;

FIG. 2 illustrates a plan view of the reaction vessel of FIG. 1 with the cover removed;

FIG. 3 illustrates a view taken on line III—III of FIG. 4 of a modified reaction vessel in accordance with the invention;

FIG. 4 illustrates a plan view of the reaction vessel of FIG. 3 with the cover removed;

Figure 7:
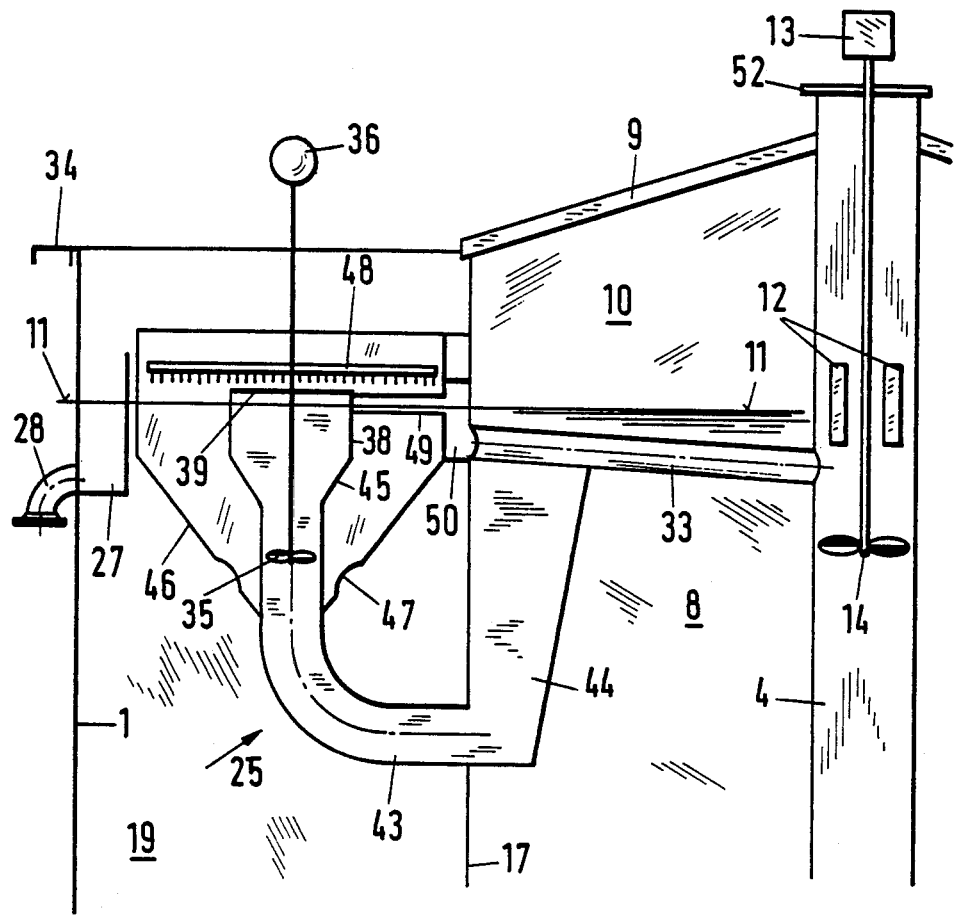

FIG. 7 illustrates a view to an enlarged scale of a conveying means for delivering liquid/biomass mixture from the reaction vessel to the sub-chamber in accordance with the invention Referring to FIGS. 1 and 2, the reaction vessel 1 is constructed of cylindrical shape and is made, for example, of steel plate having an edge reinforcement 34, as shown in FIG. 2, extending around the top edge. In addition, a sludge discharge spigot 2 and a manhole 3 are provided in the wall of the cylindrical vessel 1.

The vessel 1 includes a reaction chamber 8 for receiving contaminated liquid, such as sewage. To this end, a central supply or circulating tube 4 extends into and communicates with the reaction chamber 8 at opposite ends. As indicated in FIG. 1, the central tube 4 terminates slightly above the bottom of the chamber 8 and is secured in a base lattice structure 5 so that exit orifices 6 are formed for the supplied or circulated liquid. In addition, a deflector-like, for example a conical, baffle 7 is disposed in each orifice 6.

A cover 9 is disposed on the vessel 1 in order to close off the reaction chamber 8 from the surrounding environment. In addition, a gas chamber 10 is formed between the reaction chamber 8 and the cover 9 and is likewise also sealed from the surrounding environment. A gas discharge 13 is also provided in the cover 9 in order to vent the gas evolved from a contaminated liquid in the reaction chamber 8 to the surrounding environment. As indicated in FIG. 1, the gas chamber 10 extends from the height of the liquid level 11, that is, the interface between the liquid in the reaction chamber 8 and the gas chamber 10.

The supply tube 4 is also provided with orifices 12 at the upper end at the liquid level 11 in order to provide for the circulation of liquid. As indicated in FIG. 1, the orifices 12 extend to some extent into the gas chamber 10 so that reaction gases can pass through the top part of the tube 4 in order to leave the vessel 1 by way of the gas discharge 13.

Referring to FIG. 1, a circulating means is provided in the tube 4 for circulating liquid through the tube 4. This circulating means includes an agitator 15 which is driven by a motor 14 and which serves to convey and circulate the liquid into and through the tube 4. As indicated, the agitator 15 is introduced from the top through a gas-tight cover 52 at the upper end of the tube 4. In addition, a feed line 16 for the raw contaminated liquid to be treated also extends into the central tube 4 at the top end.

A partition 17 which is in the form of an annular ring which is concentric to the tube 4 and vessel 1 is disposed near the liquid level 11, i.e. at the interface between the reaction chamber 8 and the gas chamber 10 and at a distance from the cylindrical surface of the vessel 1. This partition 17 is supported by a number of struts 18, or the like, which also serves as a support for the cover 9. In addition, the partition 17 serves to separate an annular sub-chamber 19 from the reaction chamber 8. This sub-chamber 19 is disposed adjacent to the interface between the reaction chamber 8 and the gas chamber 10, i.e. adjacent the liquid level 11 in order to receive liquid and biomass from the reaction chamber 8 as described below.

Referring to FIGS. 1 and 2, means are provided in the sub-chamber 19 for separating biomass from the liquid in the liquid/biomass mixture delivered to the sub-chamber 19 via a conveying means 25. The separating means includes a plurality of lamellar flowbacks 20 of conventional structure and operation which are carried by the struts 18 and which are distributed about the periphery of the sub-chamber 19. In FIGS. 1 and 2 one sludge pocket of annular form is existing. In addition, the sub-chamber 19 is closed at the bottom by funnel-like sludge pockets 21 which are formed by two inclined plates 22, 23 with a sludge orifice 24 serving to return sludge to the reaction chamber 8. As indicated in FIG. 2, each conveying means 25 for conveying the liquid/biomass mixture to the sub-chamber 19 is disposed between a pair of lamellar flowbacks 20.

Referring to FIGS. 1 and 2, a collecting trough 26 is disposed at the top and inside of each flowback 20 and communicates via a small transverse trough 29 with a circular discharge trough 27 in order to receive and remove clean liquid which has been separated by the lamellar flowbacks 20. As indicated in FIG. 1, a discharge spigot 28 is connected to the circular discharge trough 27 for connection to a clean liquid outlet line (not shown).

Referring to FIGS. 1 and 2 a peripheral catwalk 30 which is diagrammatically shown extends around the sub-chamber 19 in order to provide access to the open end of the sub-chamber 19. In addition, a ladder 31 is connected to the peripheral catwalk 30 at a suitable point on the periphery. In addition, a second catwalk 32, also shown diagrammatically, extends radially into the center of the vessel 1 for access to the motor 14 for servicing and checking.

Referring to FIG. 7, the conveying means 25 for conveying the liquid/biomass mixture from the reaction chamber 8 to the sub-chamber 19 includes a tube bend 43 which extends through the partition 17 to an intake funnel 44 which dips into the liquid present in the reaction chamber 8 below the liquid level 11. Thus, the intake funnel 44 is filled with the liquid/biomass mixture which has been treated in the reaction chamber in known manner and which requires separation. In addition, an agitator 35 extends into the tube bend and is driven by a motor 36 located above the sub-chamber 19. This agitator 35 serves to draw the liquid/biomass mixture from the intake funnel 44 into and upwardly through the tube bend 43. To this end, the tube bend 43 extends to a funnel-shaped section 45 which terminates in a cylindrical section 38 having an overflow edge 39.

A funnel shaped surface sludge separator 46 extends concentrically around the cylindrically shaped section 38 of the tube bend 43 to receive the liquid/biomass mixture under gravity. As indicated, the separator 46 is formed with a plurality of orifices 47 through which the conveyed mixture can pass into the sub-chamber 19 and, therefore, into the lamellar flowbacks 20. This separator 46 serves to still the delivery from the agitator 35 and to separate surface sludge. The separator 46 also provides additional degassing of the mixture, for example to atmosphere in the example shown.

In order to boost sludge separation and degassing, a rotatable clearing device in the form of a rake mechanism 48 is disposed in concentric relation to the separator 46 in order to co-rotate with the agitator 35. A radial trough 49 also extends from the cylindrical section 38 to a sump 50 from which a return line 33 extends to the central tube 4 or the reaction chamber 8. During rotation of the rake mechanism 48, surface sludge is removed into the radial trough 49 and from there into the sump 50 for return through the line 33 to the central tube 4 or reaction chamber 8.

As indicated in FIG. 2, the conveying means 25 is mounted and retained on two rail-like supports 51 which extend radially between the vessel 1 and the partition 17.

The conveying means 25 may have a variable and adjustable capacity. To this end, the agitator 35 which is in the form of a propeller can be driven at greater or less speed via the motor 36.

As indicated in FIGS. 1 and 7, the return lines 33 extend at a slight downwards inclination from each conveying means 25 in order to return the surface sludge under gravity to the central tube 4.

In operation, the reaction vessel serves to form a liquid/biomass mixture of the raw contaminated liquid, e.g. sewage, which is delivered via the supply lines 16 and central tube 4 within the reaction chamber 8. Thereafter, the vessel separates the mixture into clean liquid, biomass and gaseous reaction products, particularly, methane and carbon dioxide.

During operation, the gaseous reaction products evolve from the mixture in the reaction chamber 8 into the gas chamber 10 above the liquid level 11 and are vented through the spigot 13. In addition, each conveying means 25 conveys and distributes the liquid/biomass mixture via an intake trough 44 and tube bend 43 into a separator 46 and, thence, into the sub-chamber 19. Any gas which is evolved at this time is vented directly to the atmosphere via the open end of the sub-chamber 19. In addition, surface-sludge can be removed via a rake mechanism 48 for return to the reaction chamber 8 via the return lines 33.

After the liquid/biomass mixture is delivered into the sub-chamber 19, the mixture flows to the respective lamellar flowbacks 20 for separation, in known manner, into clean liquid and biomass. The liquid then flows into troughs 26 and is conveyed into the circular trough 27 for discharge through the liquid discharge spigot 28. During this time, the sludge falls under gravity into the sludge pockets 21 and is discharged directly through the orifices 24 and to the reaction chamber 8.

Referring to FIGS. 3 and 4 which are strongly schematized and wherein like reference characters indicate like parts as above, a pair of partitions 17 extend diametrically over the diameter of the vessel 1. As indicated in FIG. 3, each partition 17 abuts against the cover 9 at the upper end so as to separate a sub-chamber 19 from the reaction chamber 8. In addition, a pair of lamellar flowbacks 20 are disposed and suitably supported radially by brackets and/or struts (not shown) within the sub-chamber. A conveying means 25 is also disposed between the flowbacks 20 at the center of the sub-chamber 19. As above, the conveying means 25 is in the form of an agitator 35 in the form of a propeller which is driven by a motor 36. As indicated in FIG. 3, the upper end of the sub-chamber may be open and accessible.

The conveying means 25 rests on a central column 37 which extends upwardly from the floor of a vessel 1 and which merges into a cylindrical section 38 which extends around the agitator 35 and terminates in an overflow edge 39 at the top. As indicated in FIGS. 3 and 4, pipes 40 serve to communicate the interior of the cylinder 38 in flow communication with the reaction chamber 8 below the agitator 35. During operation, the agitator 35 intakes treated liquid/biomass mixture for separation through the pipes 40 and delivers the mixture upwardly over the overflow edge 39 into the sub-chamber 19. As indicated by the arrows in FIG. 3, the mixture thereafter enters the lamellar flowbacks 20 upwardly for separation of the liquid and biomass.

As above, the clean liquid which is dispensed from the flowbacks is conveyed via radially disposed troughs 26 at the top end inside of each flowback 20 to a peripheral trough and removed in a manner similar to that described above through a suitable discharge spigot (not shown). During this time, the biomass falls under gravity into a sludge pocket 21 for return to the reaction chamber 8.

Referring to FIG. 4, the raw liquid for treatment is supplied to the vessel 1 by way of two feed lines 41 which are disposed preferably near the bottom of the vessel 1.

Figure 5:
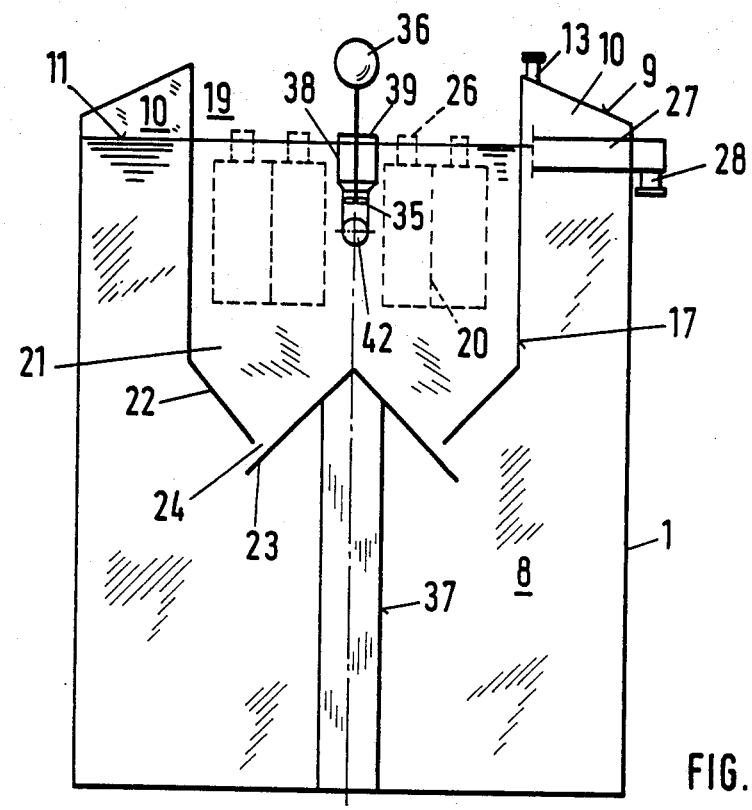
FIG. 5 illustrates a view taken on line V—V of FIG. 6 of a further modified reaction vessel in accordance with the invention.
Figure 6:
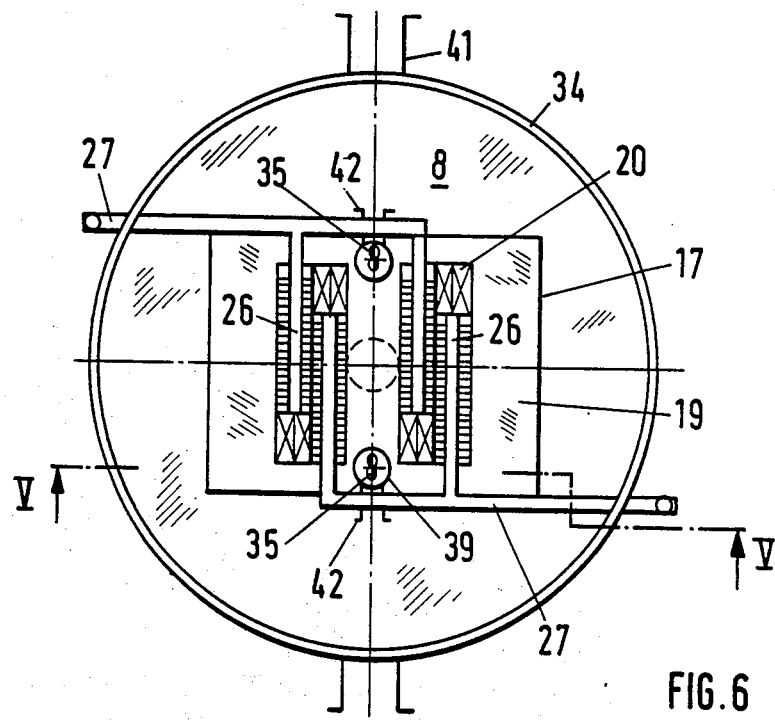
FIG. 6 illustrates a plan view of the reaction vessel shown in FIG. 5.

Referring to the likewise strongly schematized FIGS. 5 and 6, wherein like reference characters indicate like parts as above, the partition 17 is constructed so as to define a rectangular shaped sub-chamber 19 which is disposed centrally of the reaction chamber 8. The conveying means 25 of this embodiment have two agitators 35 which communicate on the intake side with the reaction chamber 8 by way of tube bends 42 which extend to the partitions 17. In this embodiment, the liquid/biomass mixture to be separated is conveyed by the agitators 35 and is distributed over the respective overflow edges 39 to the lamellar flowbacks 20. The operation of this embodiment is similar to those as described above.

The invention thus provides a reaction vessel which is of relatively simple construction and which does not require backwashing in order to clean a packed bed. Futher, the reaction vessel does not have any adverse effect on the careful treatment of a contaminated liquid so far as the anaerobic biomass is concerned, which biomass is, of course, delicate and slow to regenerate.

The invention further provides a reaction vessel which employs a minimum of parts and which is relatively easy to service and maintain.

The invention also provides a methane reactor in which the separation of an anaerobically treated mixture into pure liquid, gases and biomass is intergrated. As such, the reactor is a compact closed unit requiring no ancillary units or backwashing facilities.

Further, the invention provides conveying means which can be used for internal circulation and metered equal distribution among the various lamellar flowbacks of the mixture which has been treated and which requires separation.

We claim:

1. A reaction vessel for anaerobic treatment of contaminated liquids comprising
   a reaction chamber for receiving contaminated liquid;
   a gas chamber above said reaction chamber and sealed from the surrounding environment;
   an annular sub-chamber adjacent an interface between said reaction chamber and said gas chamber for receiving liquid and biomass from said reaction chamber;
   an annular ring separating said sub-chamber from said reaction chamber; and
   at least one lamellar flowback in said sub-chamber for separating biomass from the liquid in said sub-chamber.

2. A reaction vessel as set forth in claim 1 which further comprises a central supply tube extending into and communicating with said reaction chamber at opposite ends and circulating means in said tube for circulating the liquid through said tube.

3. A reaction vessel as set forth in claim 1 wherein said sub-chamber is open at a top end.

4. A reaction vessel as set forth in claim 1 which further comprises at least one funnel-shaped sludge pocket separating a bottom end of said sub-chamber from said reaction chamber, said pocket having sludge return orifices communicating directly with said reaction chamber.

5. A reaction vessel as set forth in claim 1 which further comprises means for conveying and distributing a liquid/biomass mixture from said reaction chamber to said lamellar flowback.

6. A reaction vessel as set forth in claim 5 which further comprises a peripheral vessel wall and wherein said ring is disposed in spaced relation to said wall with said flowbacks peripherally disposed between said ring and said wall and with each conveying means disposed between a respective pair of said flowbacks.

7. A reaction vessel as set forth in claim 5 wherein each conveying means has a variable and adjustable capacity.

8. A reaction vessel as set forth in claim 5 wherein each conveying means includes a propeller.

9. A reaction vessel as set forth in claim 5 which further comprises a central tube extending into and communicating with said reaction chamber at opposite ends, circulating means in said tube for circulating liquid therethrough, a surface sludge separator disposed downstream of said conveying means for separating sludge from the liquid/biomass mixture and a return tube extending from said separator to said central tube for returning separated sludge to said reaction chamber.

10. A reaction vessel as set forth in claim 9 which further comprises a rotatable clearing device concentric to said sludge separator for removing sludge therefrom into said return tube.

11. A reaction vessel for anaerobic treatment of contaminated liquid comprising
   a reaction chamber for receiving contaminated liquid comprising
   a gas chamber above said reaction chamber for receiving gas evolved from contaminated liquid in said reaction chamber;
   an annular sub-chamber disposed about an interface between said reaction chamber and said gas chamber for receiving a mixture of liquid and a biomass from said reaction chamber; and
   an annular ring separating said sub-chamber from said reaction chamber; and
   means in said sub-chamber for separating biomass from the liquid in the mixture in said sub-chamber.

12. A reaction vessel as set forth in claim 11 which further comprises at least one conveying means between said reaction chamber and said sub-chamber for conveying a mixture of liquid and biomass from said reaction chamber to said sub-chamber.

13. A reaction vessel as set forth in claim 12 wherein said conveying means includes an overflow edge for a flow of the conveying mixture into said sub-chamber.

14. A reaction vessel as set forth in claim 13 wherein said separating means in said sub-chamber includes at least one flowback for separating biomass from liquid, and which further comprises a liquid collecting trough at the top and inside of said flowback for receiving liquid therefrom and a sludge pocket below said flowback and closing a bottom of said sub-chamber and communicating with said reaction chamber to return sludge to said reaction chamber.

15. A reaction vessel as set forth in claim 13 wherein said conveying means includes a separator for separating surface sludge from the conveyed mixture upstream of said sub-chamber and a return line between said separator and said reaction chamber for returning separated surface sludge to said reaction chamber.

16. A reaction vessel for anaerobic treatment of contaminated liquid comprising
   a reaction chamber for receiving contaminated liquid;
   a gas chamber above said reaction chamber for receiving gas evolved from contaminated liquid in said reaction chamber;
   a sub-chamber diametrically disposed across said reaction chamber at an interface between said reaction chamber and said gas chamber for receiving a mixture of liquid and a biomass from said reaction chamber;
   a pair of parallel partitions separating said sub-chamber from said reaction chamber; and
   means in said sub-chamber for separating biomass from the liquid in the mixture in said sub-chamber.

17. A reaction vessel as set forth in claim 16 which further comprises a centrally disposed conveying means between said reaction chamber and said sub-chamber for conveying a mixture of liquid and biomass from said reaction chamber to said sub-chamber.

18. A reaction vessel for anaerobic treatment of contaminated liquid comprising
   a reaction chamber for receiving contaminated liquid;
   a gas chamber above said reaction chamber for receiving gas evolved from contaminated liquid in said reaction chamber;
   a sub-chamber of reactangular shape disposed centrally of said reaction chamber at an interface between said reaction chamber and said gas chamber for receiving a mixture of liquid and a biomass from said reaction chamber;
   a pair of parallel partitions separating said sub-chamber from said reaction chamber; and
   means in said sub-chamber for separating biomass from the liquid in the mixture in said sub-chamber.

19. A reaction vessel as set forth in claim 18 which further comprises a pair of conveying means between said reaction chamber and said sub-chamber for conveying a mixture of liquid and biomass from said reaction chamber to said sub-chamber.

* * * * *